United States Patent [19]

Pelc

[11] Patent Number: 4,581,581
[45] Date of Patent: Apr. 8, 1986

[54] METHOD OF PROJECTION RECONSTRUCTION IMAGING WITH REDUCED SENSITIVITY TO MOTION-RELATED ARTIFACTS

[75] Inventor: Norbert J. Pelc, Wauwatosa, Wis.

[73] Assignee: General Electric Company, Milwaukee, Wis.

[21] Appl. No.: 509,561

[22] Filed: Jun. 30, 1983

[51] Int. Cl.$^4$ .................................................. G01R 33/20
[52] U.S. Cl. ........................................ 324/309; 378/9; 324/307
[58] Field of Search ............... 324/300, 307, 311, 309, 324/318, 314; 378/9, 19, 92; 364/414; 73/619; 128/653

[56] References Cited

U.S. PATENT DOCUMENTS 4,129,783  12/1978  Houston ................................. 378/9
4,313,163  1/1982  Mizutani ............................. 364/414
4,333,053  6/1982  Harrison ............................. 324/309

*Primary Examiner*—Michael J. Tokar
*Attorney, Agent, or Firm*—Alexander M. Gerasimow; Douglas E. Stoner

[57] ABSTRACT

A method is provided for imaging a transverse slice of an object with reduced sensitivity to image artifacts due to object motion during the scan. The method utilizes projection measurements corresponding to at least 180° scan of the slice. The measurements are taken sequentially for views that are adjacent in angle such that measurements which are at the extremes of the scan angle are nevertheless measured at points close in time, reducing inconsistencies therebetween. The method is applicable to a number of modalities utilizing parallel-ray and fan-beam geometries, such as NMR and ultrasound, respectively.

22 Claims, 5 Drawing Figures

METHOD OF PROJECTION RECONSTRUCTION IMAGING WITH REDUCED SENSITIVITY TO MOTION-RELATED ARTIFACTS

BACKGROUND OF THE INVENTION

This invention relates to methods of collecting projection measurements at a plurality of angles through an object slice, which measurements are used to construct an image of the slice. More specifically, the invention relates to such methods which exhibit reduced sensitivity to motion-related artifacts resulting from object motion during the projection measurement acquisition process. The method has applicability to modalitites utilizing parallel-ray or fan-beam scan geometries. The preferred embodiment will be described with respect to nuclear magnetic resonance (NMR) imaging.

The nuclear magnetic resonance phenomenon occurs in atomic nuclei having an odd number of protons and-/or nuetrons. Due to the spin of the protons and the neutrons, each such nucleus exhibits a magnetic moment, such that when an object composed of such nuclei is placed in a static homogeneous magnetic field, $B_o$, a greater number of the nuclear magnetic moments align with the field to produce a net macroscopic magnetization, M, in the direction of the field. Under the influence of this field, the magnetic moments precess about the axis of the field. The frequency at which the nuclei precess is dependent on the strength of the applied magnetic field and on the nuclei characteristics. The frequency of precession, $\omega$, is referred to as the Larmor frequency and is given by the equation $\omega = \gamma B$, in which $\gamma$ is the gyromagnetic ratio which is constant for each NMR isotope, and B is the strength of the applied magnetic field. This field may include the $B_o$ field as well as magnetic-field gradients which are typically superimposed thereon. It will be recognized, therefore, that the frequency at which the nuclei precess is primarily dependent on the strength of the magnetic field B, and increases with increasing field strength.

It is possible to change the orientation of magnetization M (normally directed along field $B_o$) relative to the direction of the $B_o$ magnetic field by the application of an oscillating magnetic field which is most advantageously applied by irradiating the object with radio frequency (RF) pulses whose frequency is the same or nearly so as the precession frequency $\omega$. Radio-frequency pulses are typically applied in a plane orthogonal to the direction of the $B_o$ field. The resulting magnetic field $B_l$, resulting from the application of the radio-frequency pulses, causes the magnetization M to precess about the direction of the $B_l$ field farther and farther away from the Z axis (arbitrarily assumed to be the direction of the $B_o$ field). The extent of rotation of magnetization M from the direction of the $B_o$ field is dependent on the intensity and the duration of the RF pulses. A 90° RF pulse, for example, causes magnetization M to depart 90° from the direction of the $B_o$ field into the X-Y plane defined by the X- and Y-axes of the Cartesian coordinate system which in NMR systems is frequently assumed to be rotating at the resonant frequency $\omega$. The rotation of the magnetization M into the transverse X-Y plane creates therein a transverse magnetization which is capable of inducing a signal current in an appropriately positioned RF pickup coil, as is well known in the art. The amplitude of the induced signal decreases as the nuclear spins producing the signal dephase or lose their correlation and as the precessing transverse magnetization M returns to its equilibrium state along the $B_o$ field. The observed signal is frequently referred to as the NMR signal, or as the free-induction decay (FID) signal. Another type of RF pulse which is frequently utilized in NMR is a 180° RF pulse which causes magnetization M to rotate by 180° from its original direction (from the positive Z-axis direction to the negative Z-axis dircetion, for example). For this reason, the 180° RF pulse is frequently referred to as the inverting pulse. As will be described hereinafter, 180° RF pulses are frequently utilized to create spin-echo signals. It should be noted that a 90° or a 180° RF pulse will rotate magnetization M through the corresponding number of degrees from any initial direction of magnetization M, provided $B_l$ is perpendicular to M.

It is possible to distinguish NMR signals arising from different spatial position in the sample by changing their respective resonant frequencies. If one or more magnetic-field gradients of sufficient strength to spread out the NMR signal spectrum are applied to the sample, each nuclear spin along the direction of the gradient experiences a different magnetic field strength and, hence, resonates at a different frequency from that of the nuclear spins at other positions along the gradient direction, as predicted by the Larmor equation. Nuclei situated along lines perpendicular to direction of the gradient have the same resonant frequency and their contributions will be superimposed. Thus, the Fourier transform of the measured signal in the presence of a magnetic-field gradient represents a projection in the direction perpendicular to the gradient. In NMR imaging utilizing multiple-angle-projection reconstruction, the gradient direction is varied over a plurality of angles to cover at least a 180° arc in the imaging sample. The NMR signal observed for each gradient direction is Fourier transformed to determine the projections of the object. These projections are then reconstructed into images using well-known techniques, such as the filtered-back-projection technique utilized in X-ray computerized tomography.

In the image-reconstruction process, the projections measured at angles separated by a multiple of 180° in a given scan (either 180° or 360°) mathematically contain identical information about the object. However, the projection angle in the prior art methods is varied monotonically through the angular scan range. Thus, the projections measured at the beginning and end of the scan, in a 180° scan, for example, represent projections along directions that are approximately 180° apart and so should be quite similar. However, since they were measured at opposite ends of the scan time, they may be different if the object moved during the scan. Such differences manifest themselves as streak artifacts in the reconstructed images approximately in the direction of the first (and last) projection measurement. It will be recognized by those skilled in the art that view measurements which are adjacent in view angle within a scan must also be substantially consistent to avoid streak artifacts. It is the principal object of the invention to provide a method in which the sensitivity to such inconsistencies in projection measurement within a scan is reduced thereby to improve image quality.

SUMMARY OF THE INVENTION

In accordance with the invention, a method is provided for imaging a slice of an object undergoing examination with reduced sensitivity to motion-induced image artifacts. The method utilizes projection measurements corresponding to at least a 180° scan of the slice. The pair of projection measurements at opposite angular extremes of the scan are taken successively close in time so as to reduce inconsistencies therebetween. The remaining ones of the plurality of measurements are taken in an oscillatory manner for projection angles between the opposite scan extremes.

Application of the method is disclosed and claimed for parallel-beam and fan-beam projections, such as those useful in NMR and ultrasound imaging, respectively.

BRIEF DESCRIPTION OF THE DRAWINGS

The features of the invention believed to be novel are set forth with particularly in the appended claims. The invention itself, however, both as to its organization and method of operation, together with further objects and advantages thereof, may best be understood by reference to the following description taken in conjunction with the accompanying drawings in which:

DETAILED DESCRIPTION OF THE INVENTION

Figure 1:
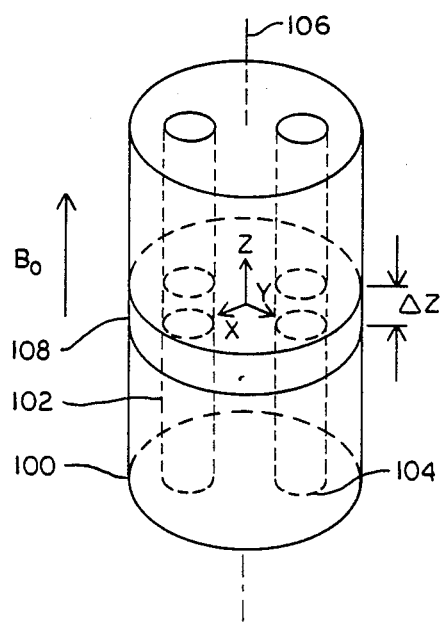
FIG. 1 illustrates an NMR sample situated in a static magnetic field and having a planar slice defined therein by selective excitation.

A conventional multiple-angle-projection-reconstruction method using NMR will now be described with reference to FIGS. 1 and 2. FIG. 1 depicts a heterogeneous sample 100, having internal features 102 and 104, positioned in a static homogeneous magnetic field $B_o$ directed in the positive Z-axis direction of a conventional Caresian coordinate system. The Z axis is selected to be coincident with a cylindrical axis 106 of the sample. The origin of the coordinate system is taken to be the center on the sample, which is also at the center of the thin planar slab or imaging slice 108 defined in sample 100 and having a thickness $\Delta Z$.

Magnetic field $B_o$ is applied during the entire NMR experiment and accordingly is omitted from all of the gigures dipicting NMR pulse sequences.

Figure 2:
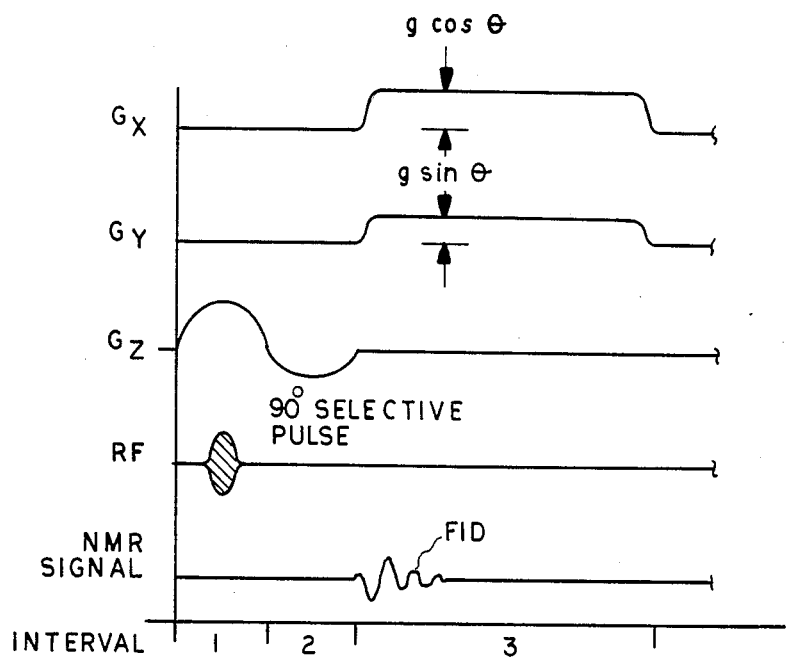
FIG. 2 depicts a multiple-angle projection reconstruction NMR pulse sequence with respect to which the preferred embodiment of the invention is disclosed.

Referring now to FIG. 2, spatial localization of the NMR signal to that produced by nuclear spins situated in imaging slice 108 is accomplished during interval 1, indicated along the horizontal axis, by the application of a magnetic field gradient $G_z$ having the form $$G_z(t) = \partial B_o / \partial z \quad (1)$$

The $G_z$ gradient (as well as the $G_x$ and $G_y$ gradients defined hereinafter) is selected to be constant throughout imaging volume 108, but its magnitude is typically time dependent. In the presence of the positive $G_z$ gradient pulse in interval 1, the object is irradiated with a selective 90° RF pulse. The RF pulse is amplitude modulated so as to contain a limited band of frequencies selected to excite only those nuclear spins in the thin planar slab of object 100 in which the Larmor frequencies match the applied magnetic field. In the preferred embodiment, the RF pulse is modulated by a sinc function (sin x/x) such that the profile of slice 108 is substantially rectangular. Nuclear spins situated outside slice 108 remain substantially unaffected by the RF pulse, since the pulse does not contain energy at other resonant frequencies. The "selective" nature of the 90° RF pulse is thus apparent.

The effect of the 90° RF pulse is to rotate the net magnetization M due to the nuclear spins situated in slice 108 into the transverse X-Y plane. When the Z gradient is turned off, the excited spins precess at the same frequency but are out of phase with one another due to the de-phasing effect of the $G_z$ gradient. The nuclear spins are rephased by the application in interval 2 of a negative $G_z$ gradient pulse. Typically, the time integral of the waveform of the $G_z$ gradient over interval 2 required to rephase the spins is approximately equal to the negative one half of the time integral of the $G_z$ gradient waveform in interval 1.

The resulting free-induction decay (FID) NMR signal is observed in interval 3 in the presence of simultaneously applied magnetic-field gradients $G_x$ and $G_y$ directed in the X- and Y-axes directions, respectively. The $G_x$ and $G_y$ gradients are defined in interval 3 as $$G_x(t) = \partial B_o / \partial y \quad (2)$$

$$G_y(t) = \partial B_o / \partial y. \quad (3)$$

The magnitudes of the $G_x$ and $G_y$ gradients in interval 3 determine the projection angle $\theta$. The magnitude of the $G_x$ gradient is made proportional to the cosine of the projection angle while the magnitude of the $G_y$ gradient is made proportional to the sine of the projection angle. The $G_x$ and $G_y$ gradients add vectorially to produce a resultant gradient in the imaging plane at a direction $\theta$ with respect to the Y axis, as illustrated schematically in FIG. 3 by arrows 300, 302, 304, 306, and 308. In the prior-art methods, the projection angle $\theta$ is progressively incremented and the magnitudes of the $G_x$ and $G_y$ gradients adjusted to change the orientation of the radial gradient so as to obtain projection data from at least a 180° arc within imaging slice 108. The pulse sequence comprising intervals 1, 2, and 3 in FIG. 2 may be repeated more than once, and the results for each angle $\theta$ averaged prior to advancing the angle so as to improve the signal-to-noise ratio of the projections.

Figure 3:
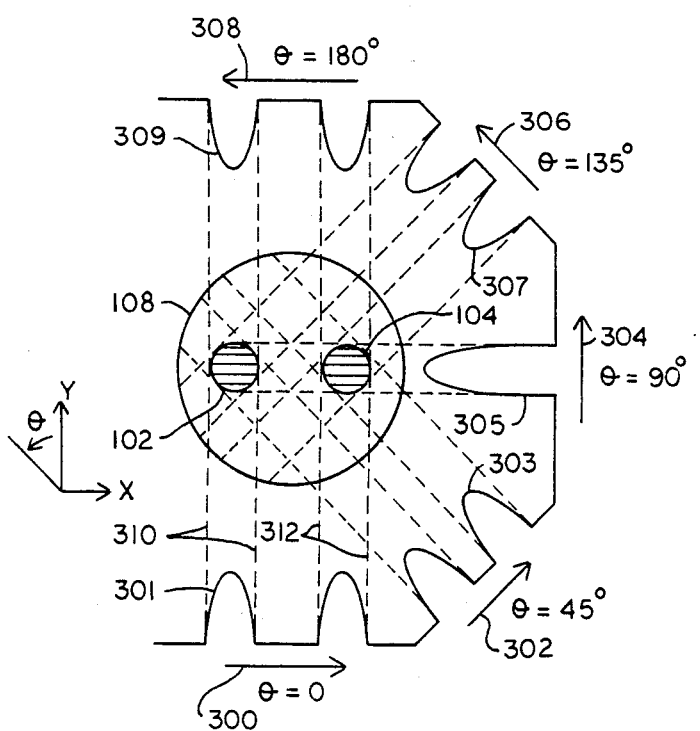
FIG. 3 depicts schematically the method of image reconstruction from back projections utilizing NMR.

The Fourier transform of the FID signal observed in interval 3 of FIG. 2 represents a projection of the imaging slice onto a line having the same direction within slice 108 as the gradient. This may be best visualized by recognizing the fact that Fourier transformation of the time domain FID signal into the frequency domain yields the magnitude of the signal at each frequency and, therefore, at each location with respect to the direction of the gradient. The nuclei situated along each line through slice 108, perpendicular to the direction of the gradient, have the same resonant frequency. Each such line is referred to as an isochromat and defines a projection onto a point of all points domprising an isochromat. FIG. 3 illustrate Fourier transform projections 301, 303, 305, 307, and 309 of internal sample features 102 and 104 (FIG. 1) associated with radial gradients 300, 302, 304, 306, and 308, respectively.

The image of slice 108 is reconstructed from all of the projections using well-known reconstruction methods, such as filtered-back projection commonly utilized in computerized tomography.

Referring again to FIG. 3, it will be recognized that the projection data obtained by means of projection 300 at a projection angle $\theta=0$ is substantially equivalent to the information obtained by projection 308 at an angle of 180°. In practice, if the first projectin is measured at an angle $\theta_o$ with respect to some reference direction and rotation is in the direction such that the projection angle $\theta$ increases by an incremental amount $\Delta\theta$ for each view, then the last view is at an angle of $\theta_o+\pi-\Delta\theta$. In the reconstruction process, the first and last views are mathematically treated as being adjacent in angle an should contain quite similar projection information about imaging slice 108. However, the first and last views are measured at opposite ends of the scan time. Therefore, it will be appreciated that the first and last views will contain equivalent information only if the object scanned remains stationary during the scan. But, if the object, such as a patient, moves during the scan, then the first and last views will contain inconsistencies which manifest themselves as streaks in the reconstructed image and in approximately the $\theta_o$ direction. Views adjacent in angle $\theta$ within the scan are measured close in time and as a result will not have significant inconsistencies.

In most X-ray computerized tomograpy scanners, the rotation of the direction of the projection is accomplished by mechanical rotation of the gantry supporting an X-ray source. In this case, projection angles must be varied monotonically (in fact, usually linearly) over time. In NMR, this need not be the case since the direction of the projection is determined electronically by energizing the gradient coils (e.g., $G_x$ and $G_y$, not shown) with currents of pre-selected amplitudes.

In accordance with the invention, reduced sensitivity to the afore-described artifacts due to measurement inconsistencies between the views at the scan extremes can be obtained by controlling the sequence in which the gradient direction is selected. One way of accomplishing this is to acquire a first projection in the middle of the angular range covered by the scan, and then vary the projection direction to the two extremes of the range simultaneously. For example, in FIG. 3, projection 304 would be the first measured projection and then sequentially adjacent projection pairs may be measured for projections 302 and 306 and then adjacent projection pairs 300 and 308. In this manner, projections 300 and 308, which lie at opposite angular extremes at the end of the scan, are in fact measured successively close in time so that any inconsistencies due to the object motion are substantially reduced. Additionally, with the inventive scan-sequence-projection measurements which are adjacent in ange within the scan, such as, for example, those on either side of the measurement at $\theta=45°$ are taken sufficiently close in time so that they are substantially free of inconsistencies. The reconstructed images utilizing such projection data exhibit reduced sensitivity to motion artifacts. It will be recognized that the sequence could also be reversed. In this case, the vies at 300 and 308 at the angular extremes at the beginning of a scan would be measured first, and the drection of the projections alternated, moving the projection angle toward the center in an osillatory manner so that projections 302 and 306 would be obtained next, and then the center projection at 304. Generally, it is desirable that successive projection measurements be taken at intervals $\Delta T$ not greater than one half of the total scan time. In the preferred embodiment, the measurements are taken at $\Delta T$, much less than the total scan time to maximize reduction of motion artifacts. In practice, many more projections are measured in order to construct an image having the desired resolution and being free of aliasing artifacts.

One exemplary embodiment of the inventive projection measurement sequence may be described in a simplified manner by assuming that $N_v$, the total number of projections, is selected to be odd and by defining $N_m=(N_v+1)/2$. The scan then begins by measuring a projection at the center of the scan at an angle $$\theta = \theta_o + \left(\frac{N_v - 1}{2}\right) \Delta\theta.$$

Subsequent projections are then measured in the following sequence:

$$\theta_o + \frac{N_v - 3}{2} \Delta\theta$$

$$\theta_o + \frac{N_v + 1}{2} \Delta\theta$$

$$\theta_o + \frac{N_v - 5}{2} \Delta\theta$$

$$\theta_o + \frac{N_v + 3}{2} \Delta\theta$$

$$\theta_o + \frac{N_v - 7}{2} \Delta\theta$$

$$\theta_o + \frac{N_v + 5}{2} \Delta\theta$$

.
.
.
$$\theta_o$$
$$\theta_o + (N_v - 1) \Delta\theta = \theta_o + \pi - \Delta\theta$$

It will be readily appreciated by those skilled in the art that this method can be implemented for either an odd or even number of projections.

Figure 4:
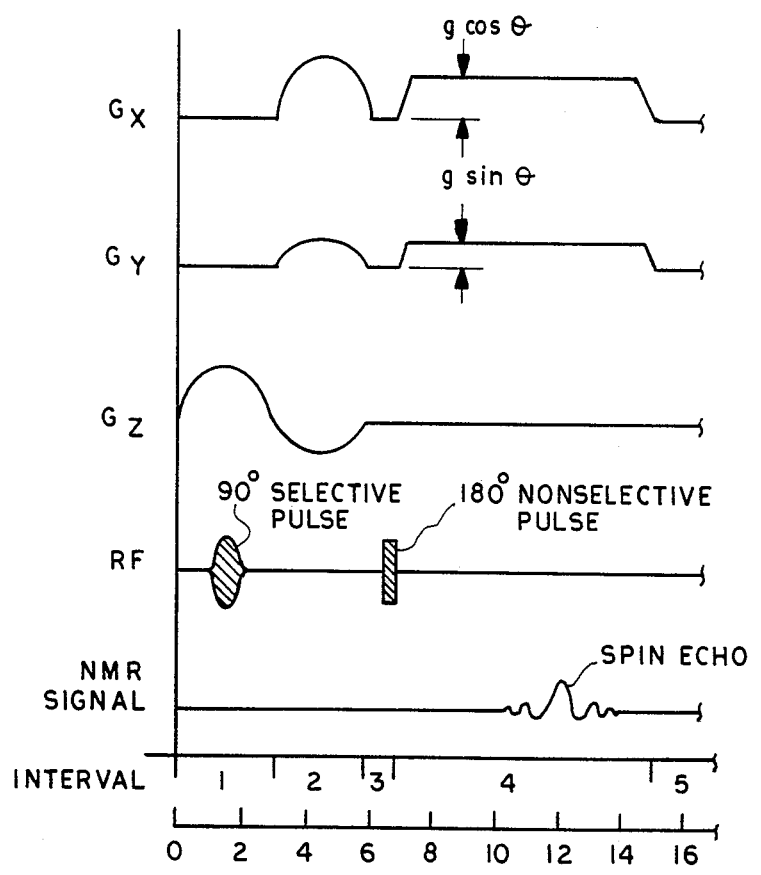
FIG. 4 illustrates an alternative multiple-angle projection reconstruction NMR pulse sequence useful with the method of the invention in which a 180° RF pulse is used to produce a spin-echo signal.

FIG. 4 depicts a preferred embodiment of the multiple-angle-projection-reconstruction technique which may be advantageously employed within the method of the invention. The pulse sequence depicted in FIG. 4 is substantially identical to that depicted in FIG. 2 but with the exception that gradients $G_x$ and $G_y$ are modified to also have an amplitude in interval 2 that is proportional to the respective amplitudes that are applied in interval 4. A 180° non-selective RF pulse is applied in interval 3. The effect of the $G_x$ and $G_y$ gradients in combination with the 180° RF pulse is to delay the occurence of the NMR signal by first de-phasing, inverting, and then re-phasing the nuclear spins in slice 108 so as to produce a spin-echo signal in interval 4 of FIG. 4.

Referring to interval 3 of FIG. 2, it will be observed that the FID signal occurs immediately upon the termination of interval 2 and at the beginning of interval 3 when gradient $G_z$ has been de-energized and gradients $G_x$ and $G_y$ have been just energized. Such conditions are not ideal for the observation of the FID signal because, even if the $G_x$ and $G_y$ magnetic-field gradients could be applied could be applied abruptly, there is still a finite time period when the exact resulting gradient is transient and its exact magnitude unknown. During this interval, spatial information is badly distorted, and then FID signal cannot normally be used. This problem is, however, overcome by the application in interval 2 of FIG. 4 of positive $G_x$ and $G_y$ gradient pulses to de-phase the nuclear spins by a predetermined amount so as to delay the occurrence of the NMR signal. The accumulated phase dispersion is reversed in interval 3 by the application of a non-selective 180° RF pulse. When the $G_x$ and $G_y$ gradients are applied in interval 4, the spins begin to re-phase and produce a spin-echo signal in interval 4 which can be observed in the period when the radial gradient is stable.

The appicability of the inventive projection sequence is not limited to the parallel-ray-projection method disclosed with reference to miltiple-angle-projection reconstruction in NMR. The invention has equal applicability to, for example, fan-beam projections such as those which may be utilized in the ultrasound scanning apparatus schematically depicted in FIG. 5. The ultrasound apparatus may comprise a plurality of ultrasound transducers 500 disposed along the circumference of a supporting member 501. The transducers are such that they can transmit a fan beam of ultrasound radiation and to convert impinging ultrasound radiation into electrical currents corresponding in intensity to the impinging ultrasonic pressure pulse. An object, such as object 502, positioned at the center of member 501 may then be scanned by transmitting an ultrasonic pulse along the fan beam whose peripheries are defined by rays A and B from a transducer such as transducer 504. Ultrasound energy passing through object 505 is then detected by transducers 514, 516, and 518 positioned opposite transmitting transducer 504. Although the projection data may be measured in terms of attenuation of ultrasound energy passing through object 502 as is done in convention computerized tomography using X-rays, it is preferable to measure the time interval between the emission and the reception of the ultrasound beam at various transducer positions which can be converted to a line integral of the speed of sound within the object. The advantage of this type of measurement is that it is less sensitive to errors due to refraction than is the attenuation method. Measurement of the time between the emission of an ultrasonic pulse by one transducer and the arrival at a set of opposed transducers can be converted into a fan-beam projection of the distribution of speed of sound within the object slice. This process is repeated a number of times to obtain the desired projections around the object. As in the NMR case, the order in which the projections are measured is determined electronically.

In accordance with the invention, rather than arranging the projection angles monotonically by energizing transducers sequentially around the circumference of structure 501, it is preferred to obtain a central projection utilizing transducer 504, for example, and then alternating between transducers 506 and 508 and then 510 and 512, etc., in order to ensure that the first and last views are obtained close in time. Thus, if the object moves during the scan, the magnitude of the inconsistencies between the first and last views is reduced and the reconstructed image will exhibit a reduced susceptability to motion artifacts.

Figure 5:
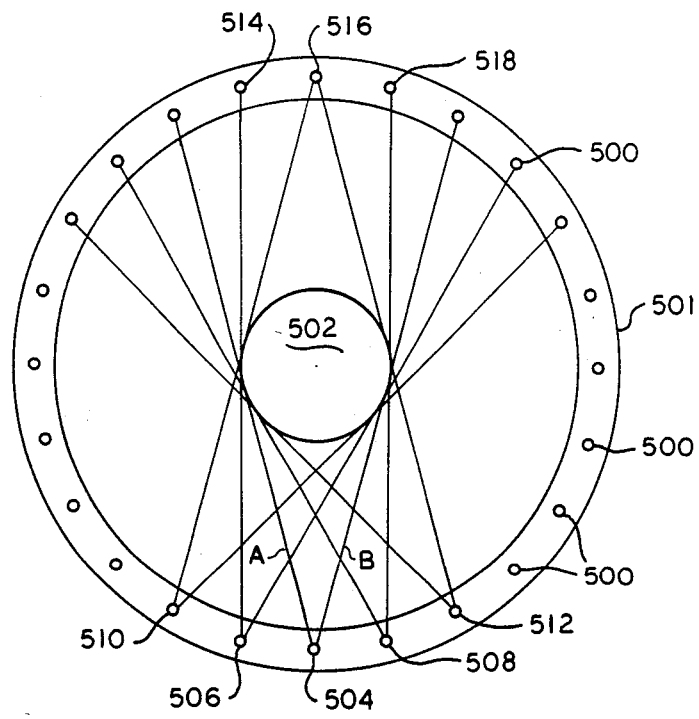
FIG. 5 illustrates schemtically the application of the method of the invention to ultrasound methods of multiple-angle-projection reconstruction utilizing ultasound fan-beams.

It will be recognized that the scanning sequence described above for ultrasound apparatus with reference to FIG. 5 may be utilized for a computerized tomography scan geometry for use with an apparatus (not shown) having, for example, a plurality of individually energizable stationary X-ray sources positioned along the circumference of a support structure similar to structure 501. In this case, in accordance with the invention, the X-ray sources would be activated to take projection measurements of an object along directions that vary in the oscillatory manner (as previously described), such that the first and last views would be obtained close in time. U.S. Pat. No. 4,129,783, assigned to the same assignee as the present invention, discloses an apparatus utilizing an array of X-ray sources disposed opposite an X-ray detector array.

From the foregoing, it will be appreciated that, in accordance with the invention, a method is provided which is easily implementable and which reduces the sensitivity to motion artifacts in modalities which utilize multiple projections to reconstruct transverse images of an object.

While this invention has been described with reference to particular embodiments and examples, other modifications and variations will occur to those skilled in the art in view of the above teachings. Accordingly, it should be understood that within the scope of the appended claims the invention may be practiced otherwise than is specifically described.

What is claimed is:

1. In a method of imaging a slice of an object undergoing examination, which method utilizes a scan composed of a plurality of projections, each of said projections measured at a predetermined point in time and at a predetermined projection angle relative to a reference direction within said slice, wherein the minimum and maximum projection angle values differ by at least 180°, the improvement wherein projections measured in following ones of a plurality of successive time segments, each of said time segments being a time interval during which at least two projections are measured and being short compared to the total scan time, include the measurement of projections at the minimum and the maximum projection angle values for projections not yet measured.

2. The method of claim 1 wherein said method comprises measuring parallel-ray projections.

3. The method of claim 2 wherein the direction of each projection measurement within said imaging slice is determined by the direction of a magnetic-field gradient.

4. The method of claim 3 wherein said imaging slice is positioned in a static homogeneous magnetic field and includes the steps of:

selectively exiting a plurality of nuclear spins situated in said imaging slice such that said nuclear spins produce an NMR signal; and observing said NMR signal in the presence of said magnetic-field gradient wherein isochromats perpendicular to the gradient direction represent projections of points along the isochromats onto said gradient.

5. The method of claim 1 wherein said method comprises measuring fan-beam projections.

6. The method of claim 5 wherein said fan beam comprises a beam of ultrasonic energy.

7. The method of claim 6 wherein said projection measurements comprise measuring the intensity o the ultrasonic energy not absorbed or scattered within said imaging slice along a plurality of ray paths within said fan beam.

8. The method of claim 6 wherein said projection measrements comprise measuring the propagation velocity of said ultrasonic beam along a plurality of ray paths within said fan beam.

9. The method of claim 6 wherein projection measurements are made to corespond to at least a 360° scan of the object.

10. The method of claim 6 wherein sid step of measuring a projection comprises the steps of:
   positioning said object in an annular array of ultrasonic transducers each capable of transmitting and receiving ultrasonic energy;
   irradiating said imaging slice with a substantially coplanar beam of ultrasonic energy produced by one of said transducers; and
   detecting the ultrasonic energy not attenuated or scattered within said slice at a plurality of transducers situated within an angle subtended by said fan beam.

11. In a method of imaging a slice of an object undergoing examination, which method utilizes a scan composed of a plurality of projections, each of said projections measured at a predetermined point in time and at a predetermined projection angle relative to a reference direction within said slice, wherein the minimum and maximum projection angle values differ by at least 180°, the improvement wherein a first one of said plurality of projections is measured at a first predetermined projection angle and wherein a second one of said plurality of projections is measured at a second predetermined projection angle and wherein predetermined ones of the remaining ones of said plurality of projections are measured in each of a plurality of successive time segments, each of said time segments being a time interval during which at least two projections are measured and being short compared to the total scan time, such that projections measured in a preceding one of said plurality of successive time segments include measurement of projections at the minimum and maximum projection angle values for the projection already measured.

12. The method of claim 11 wherein said first predetermined projection angle is approximately equal to the average of the values of said minimum and maximum projection angles.

13. The method of claim 11 wherein said second predetermined projection angle is angularly adjacent to said first projection angle.

14. The method of claim 11 wherein said method comprises measuring parallel-ray projections.

15. The method of claim 14 wherein the direction of each projection measurement within said imaging slice is determined by the direction of a magnetic-field gradient.

16. The method of claim 15 wherein said imaging slice is positioned in a static homogeneous magnetic field and includes the steps of:
   selectively exciting a plurality of nuclear spins situated in said imaging slice such that said nuclear spins produce an NMR signal; and
   observing said NMR signal in the presence of said magnetic-field gradient wherein isochromats perpendicular to the gradient direction represent projections of points along the isochromats onto said gradient.

17. The method of claim 11 wherein said method comprises measuring fan-beam projections.

18. The method of claim 17 wherein said fan beam comprises a beam of ultrasonic energy.

19. The method of claim 18 wherein said projection measurements comprise measuring the intensity of the ultrasonic energy not absorbed or scattered within said imaging slice along a plurality of ray paths within said fan beam.

20. The method of claim 18 wherein said projection measurements comprise measuring the propagation velocity of said ultrasonic beam along a plurality of ray within said fan beam.

21. The method of claim 18 wherein projection measurements are made to correspond to at least 360° scan of the object.

22. The method of claim 18 wherein said step of measuring a projection comprises the steps of:
   positioning said object in an annular array of ultrasonic transducers each capable of transmitting and receiving ultrasonic energy;
   irradiating said imaging slice with a substantially coplanar beam of ultrasonic energy produced by one of said transducers; and
   detecting the utlrasonic energy not attenuated or scattered within said slice at a plurality of transducers situated within an angle subtended by said fan beam.

* * * * *

UNITED STATES PATENT AND TRADEMARK OFFICE
CERTIFICATE OF CORRECTION

PATENT NO. : 4,581,581

DATED : April 8, 1986

INVENTOR(S) : Norbert J. Pelc

It is certified that error appears in the above-identified patent and that said Letters Patent is hereby corrected as shown below:

Col. 2, line 9, change "dircetion" to --direction--;
Col. 2, line 18, change "position" to --positions--.
Col. 3, line 8, change "osciallatory" to --oscillatory--;
Col. 3, line 34, change "schemtically" to --schematically--;
Col. 3, line 36, change "ultasound" to --ultrasound--;
Col. 3, line 47, change "Caresian" to --Cartesian--;
Col. 3, line 55, change "gigures" to --figures--.
Col. 4, line 66, change "domprising" to --comprising--;
Col. 4, line 67, change "illustrate" to --illustrates--.
Col. 5, line 58, change "ange" to --angle--;
Col. 5, line 65, change "vies" to --views--.
Col. 8, line 68, change "o" to --of--.
Col. 9, line 5, change "measrements" to --measurements--;

Col. 9, line 11, change "sid" to --said--.
Col. 10, line 32, after "ray" insert --paths--;
Col. 10, line 35, after "least" insert --a--.

Signed and Sealed this

Twenty-first Day of April, 1987

*Attest:*

DONALD J. QUIGG

*Attesting Officer*  *Commissioner of Patents and Trademarks*